(12) United States Patent
Gregar

(10) Patent No.: US 9,200,994 B2
(45) Date of Patent: Dec. 1, 2015

(54) DEVICE AND METHOD FOR SENSING APPLIED CONDITION OF A RAILROAD HANDBRAKE

(71) Applicant: Peter Gregar, Chesterton, IN (US)

(72) Inventor: Peter Gregar, Chesterton, IN (US)

(73) Assignee: WABTEC Holding Corp, Wilmerding, PA (US)

( * ) Notice: Subject to any disclaimer, the term of this patent is extended or adjusted under 35 U.S.C. 154(b) by 43 days.

(21) Appl. No.: 13/965,641

(22) Filed: Aug. 13, 2013

(65) Prior Publication Data

US 2013/0319130 A1 Dec. 5, 2013

Related U.S. Application Data

(63) Continuation of application No. 13/028,454, filed on Feb. 16, 2011, now Pat. No. 8,616,341.

(51) Int. Cl.
*B61H 13/04* (2006.01)
*G01N 3/08* (2006.01)

(52) U.S. Cl.
CPC . *G01N 3/08* (2013.01); *B61H 13/04* (2013.01)

(58) Field of Classification Search
CPC ................................. B61H 13/04; G01L 5/10
USPC ............ 188/1.11 R, 1.11 E, 33, 34, 107, 216; 246/167 R, 182 R, 182 A, 182 B; 73/826, 73/828, 829
See application file for complete search history.

(56) References Cited

U.S. PATENT DOCUMENTS

| | | | |
|---|---|---|---|
| 4,368,648 A | 1/1983 | Houseman et al. | |
| 4,714,142 A | 12/1987 | Sheperd | |
| 5,503,250 A * | 4/1996 | Schantz et al. | 188/1.11 E |
| 6,237,722 B1 * | 5/2001 | Hammond et al. | 188/1.11 R |
| 6,364,069 B1 * | 4/2002 | Ring | 188/1.11 R |
| 6,474,450 B1 | 11/2002 | Ring et al. | |
| 6,725,727 B2 * | 4/2004 | Rogers et al. | 73/828 |
| 7,757,825 B2 | 7/2010 | Michel | |
| 7,878,309 B2 | 2/2011 | Michel et al. | |
| 8,584,551 B2 * | 11/2013 | Gregar et al. | 74/506 |
| 8,616,341 B2 * | 12/2013 | Gregar | 188/34 |

* cited by examiner

*Primary Examiner* — Thomas J Williams
(74) *Attorney, Agent, or Firm* — James Ray & Assoc

(57) ABSTRACT

A device for indirectly sensing tension of a chain in a railroad handbrake includes an elongated bore formed through a holding pawl of the handbrake, sensor target attached to the holding pawl and a sensor mounted in close proximity to an upper end of the housing so as to sense the sensor target. The ratchet wheel of the handbrake positions the sensor target for operative sensing alignment with the sensor during at least partial handbrake application. A biasing member moves the sensor target away from the operative sensing alignment during handbrake release.

25 Claims, 4 Drawing Sheets

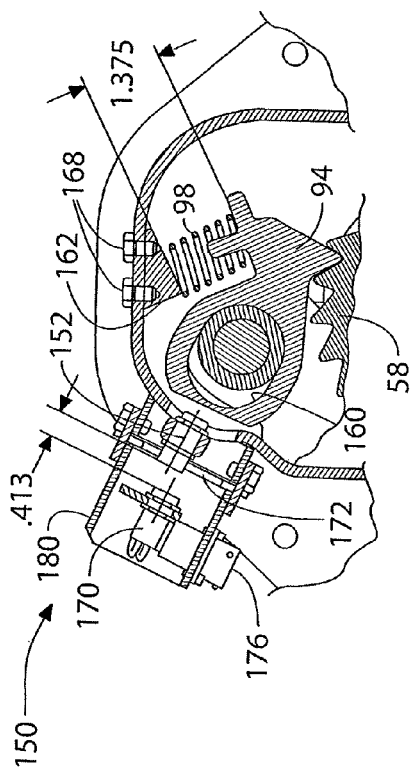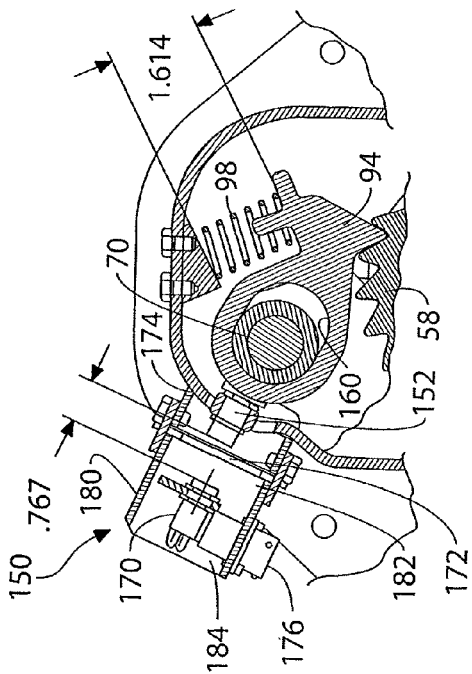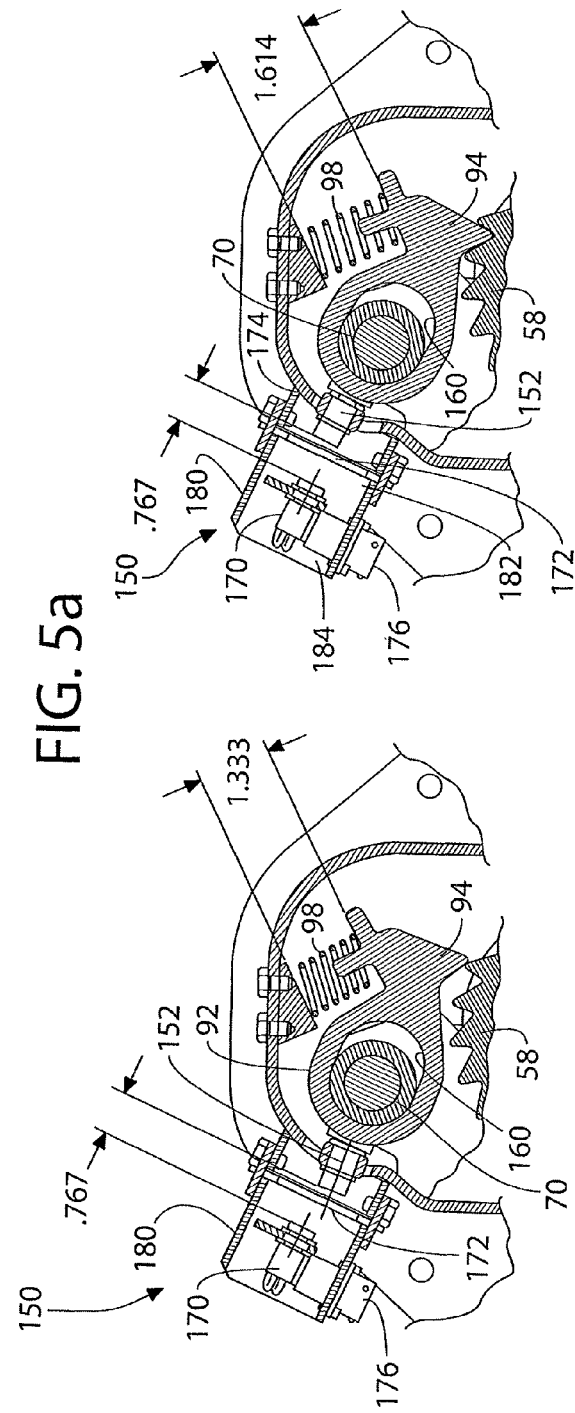
FIG. 5a
FIG. 5b
FIG. 5c

DEVICE AND METHOD FOR SENSING APPLIED CONDITION OF A RAILROAD HANDBRAKE

CROSS-REFERENCE TO RELATED APPLICATIONS

This application is a Continuation of U.S. patent application Ser. No. 13/028,454 filed Feb. 16, 2011, pending.

FIELD OF THE INVENTION

The present invention relates, in general, to railroad handbrakes and, more particularly, this invention relates to device and method for indirectly sensing tension condition of a force-producing chain of the railroad handbrake, and yet more particularly, the instant invention relates to a sensor mounted on a housing of the railroad handbrake and sensing generally linear movement of a holding pawl of the railroad handbrake in response to tension in the force-producing chain during at least partial handbrake application.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

As is generally well known, each railcar has a handbrake which utilizes a force-producing chain being manually taken-up or let-up for setting and releasing brakes of the railcar. One of the disadvantages of using handbrakes with which the instant invention is concerned is that some handbrakes within a train consist are not being released prior to train consist movement resulting in wheel lock-ups and further resulting in wheel flats that require repair or even replacement of the entire wheel.

Thus, there is a need for a device and method that can be used for determining when the tension is present in force-producing chain and, more particularly, when the force-producing chain has been at least partially set or remains at least partially set.

SUMMARY OF THE INVENTION

The invention provides chain tension sensing device for a railroad handbrake. The railroad handbrake generally includes a housing, a chain application and release mechanism at least partially disposed within the housing and a holding pawl, the holding pawl having each of a body thereof mounted for rotation and a ratchet wheel engaging portion thereof extending from the body and cooperating with a ratchet wheel of the chain application and release mechanism. The railroad handbrake further including means for biasing the ratchet wheel engaging portion for engagement with the ratchet wheel. The chain tension sensing device includes an elongated bore formed through a thickness of the body of the holding pawl so that the holding pawl is mounted for a generally linear reciprocal movement in a direction being generally transverse to a rotational axis thereof. A sensor target is provided and has a proximal end thereof disposed on and attached to an exterior surface of the body of the holding pawl. The sensor target extends in a direction being generally opposite to a direction of the ratchet wheel engaging portion of the holding pawl. The sensor target is disposed for the generally linear reciprocal movement with the body. A sensor is mounted in close proximity to an upper end of the housing and having an opening disposed in the general alignment with the sensor target. The opening is sized to receive a distal end portion of the sensor target, wherein the distal end portion enters the opening during at least partial handbrake application and exits the opening during handbrake release. An urging means is caged between an interior surface of the housing and the exterior surface of the body. The ratchet wheel moves the body of the holding pawl in a direction towards the sensor during the at least partial handbrake application and positions the distal end portion of the sensor target within the opening of the sensor in operative sensing alignment therewith. The urging means moves the body of the holding pawl in an opposite direction towards the ratchet wheel during handbrake release causing the distal end portion of the sensor target to exist the opening. The sensor generates a control signal in response to sensing or not sensing the distal end portion.

The invention also provides a method for sensing at least partially applied condition of a railroad handbrake. The method includes the step of mounting a member for a reciprocal movement in a generally linear direction during handbrake application and release. Next, mounting a sensor in close proximity to an upper end of a housing of the railroad handbrake in a position to sense the generally linear movement of the member during at least partial handbrake application. Then, moving the member in the generally linear direction during the at least partial handbrake application. Finally, sensing the generally linear movement of the member during the at least partial handbrake application.

OBJECTS OF THE INVENTION

It is, therefore, one of the primary objects of the present invention to provide a device for sensing tension condition of a force-producing chain of the railroad handbrake.

Another object of the present invention is to provide a chain tension sensing device for a railroad handbrake that includes a holding pawl movable in a direction transverse to rotational axis thereof.

Yet another object of the present invention is to provide a chain tension sensing device for a railroad handbrake that includes a sensor mounted on an upper end of the railroad handbrake housing.

A further object of the present invention is to provide a chain tension sensing device for a railroad handbrake that includes means for urging the holding pawl for engagement with a ratchet wheel of the railroad handbrake.

Yet a further object of the present invention is to provide chain tension sensing device for a railroad handbrake that is economical to manufacture.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE DRAWINGS

FIGS. 5a-5c are partial cross-sectional views illustrating operation of the chain tension sensing device of FIG. 4;

BRIEF DESCRIPTION OF THE VARIOUS EMBODIMENTS OF THE INVENTION

Figure 1:
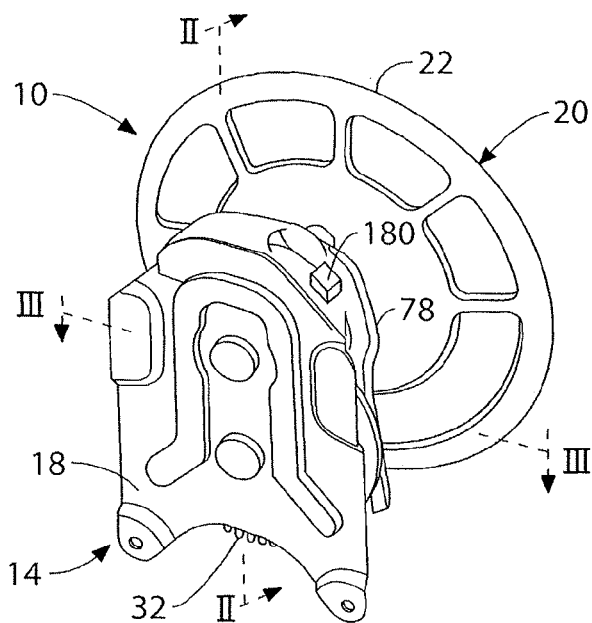
FIG. 1 is a perspective view of a railroad handbrake employing a chain tension sensing device of the claimed invention.

Prior to proceeding to the more detailed description of the present invention, it should be noted that, for the sake of clarity and understanding, identical components which have identical functions have been identified with identical reference numerals throughout the several views illustrated in the drawing figures.

The present invention describes a device and method for sensing applied condition of a railroad handbrake, generally designated as 10, which provides means to indirectly sense a condition wherein a force-producing chain of the railroad handbrake has been either taken-up or let-up during handbrake application for respectively at least partially setting or rereleasing railcar brakes.

The present invention is illustrated and described in combination with a handbrake generally described and taught in U.S. Pat. No. 4,368,648 issued to Housman et al. and owned by the assignee of the instant invention, although it will be apparent to those skilled in the relevant art that the present invention may be applied to other railroad handbrake type employing a force-producing chain and a manually operated rotating hand wheel and as such should not be interpreted as a limiting factor of the railroad handbrake of the instant invention. Teachings of U.S. Pat. No. 4,368,648 are incorporated into this document by reference thereto.

The best mode for carrying out the invention is presented in terms of its presently preferred embodiment, herein depicted within FIGS. 1 through 5C. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the instant invention can be easily incorporated into the teachings thereof.

Figure 3:
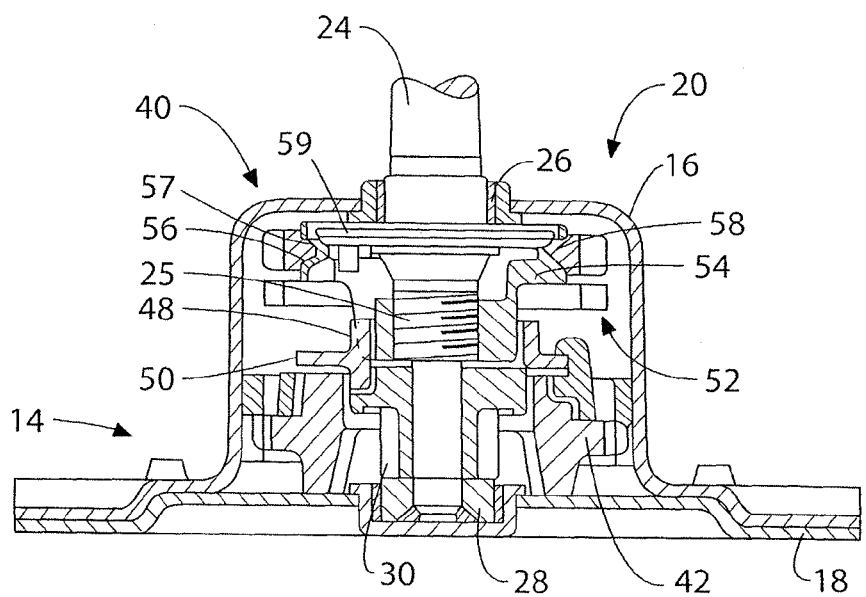
FIG. 3 is a cross-sectional view of the railroad handbrake along lines III-III of FIG. 1.
Figure 2:
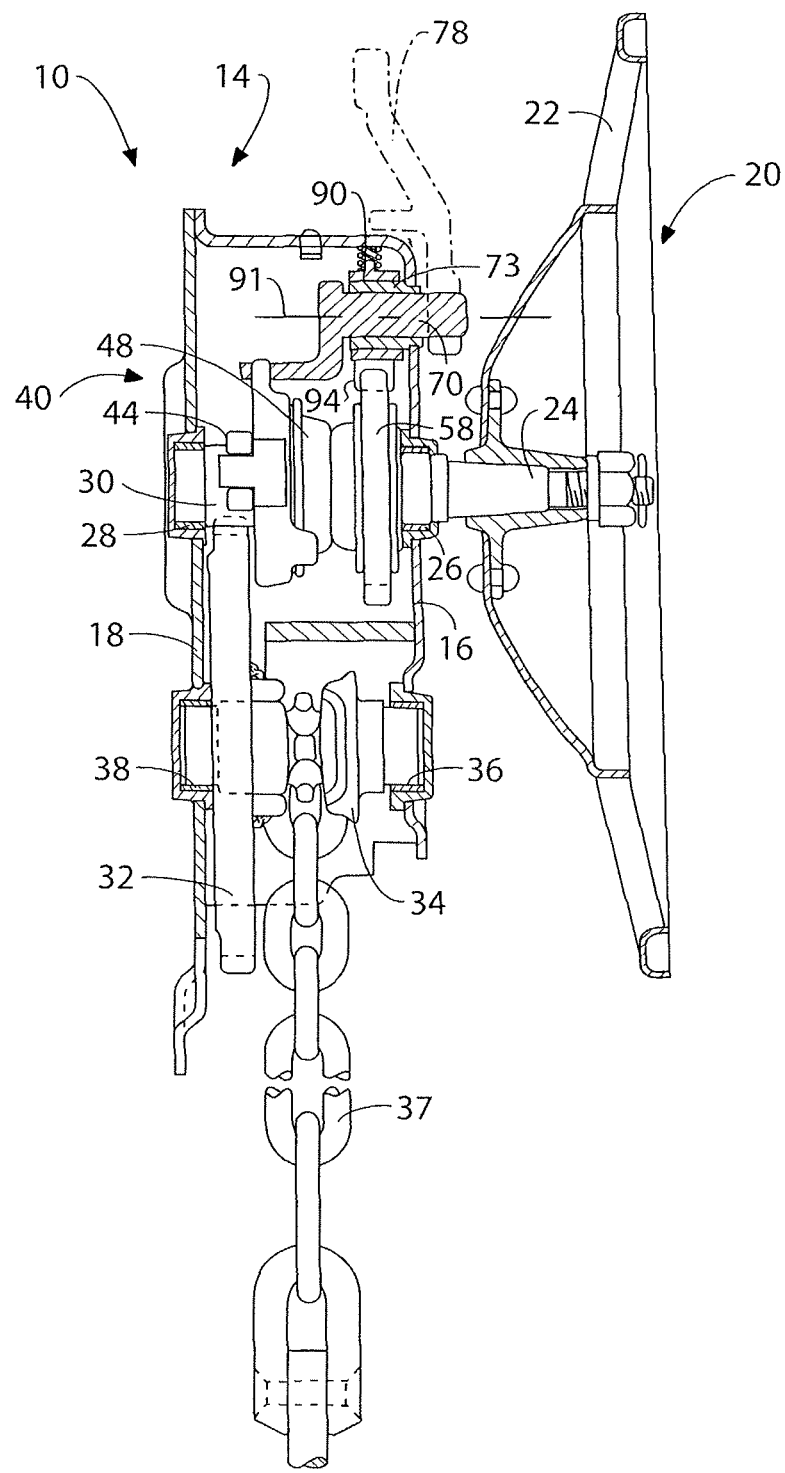
FIG. 2 is a cross-sectional view of the railroad handbrake along lines II-II of FIG. 1.

Now in a particular reference to FIGS. 1-3, and for the sake of user's reading convenience, therein is illustrated a handbrake 10 for railroad cars (not shown). Briefly, the handbrake 10 comprises a generally hollow housing, generally designated as 14, having a front plate 16 and a back plate 18. A chain application and release mechanism is provided and includes manually operable driving mechanism, generally designated as 20, which is at least partially disposed in the upper portion of housing 14 and includes a hand wheel 22 which is disposed on and secured to one end of a drive shaft 24, external to the exterior surface of the housing 14, and further being journaled for rotation in bearings 26 and 28 secured in the front plate 16 and back plate 18, respectively.

A pinion 30 is secured within the housing 14 to the drive shaft 24 for rotation therewith at the opposed end thereof adjacent bearing 28. The pinion 30 operatively engages a gear 32 for rotating a chain drum 34 journaled for rotation in bearings 36 and 38 secured on the front plate 16 and back plate 18, respectively, in the lower portion of the housing 14.

Chain drum 34 engages alternate links of a force-producing chain 37 for either taking-up or letting-out the force-producing chain 37.

Also disposed in the upper portion of the housing 14 and associated with the driving mechanism 20, is a clutch and release mechanism, generally designated as 40, which may best be seen in FIGS. 2-3. The clutch and release mechanism 40 includes an annular stationary cam member 42 restrained from both axial and rotational movement, and a movable cam member, generally designated as 44, rotatably and concentrically disposed within the stationary cam member 42. The movable cam member 44 is rotatable relative to the stationary cam member 42.

An internally splined annular clutch collar 48 is provided with an annular flange 50 and concentrically surrounds the drive shaft 24, the collar engaging with an externally splined nut, generally designated as 52, which is attached to the threaded portion 25 of the drive shaft 24. Nut 52 has a flange 54 with an annular friction surface 56 for making abutting contact with one side of a ratchet wheel 58, while the other side of the ratchet wheel 58 operatively abuts a friction surface 57 of a friction plate 59 concentrically secured to the drive shaft 24 adjacent the bearing 26. The ratchet wheel 58 is essentially a disk shaped member having annular raw of ratchet teeth disposed on a peripheral edge thereof.

A holding pawl 90 is provided and has a body 92 mounted for rotation within the housing 14 and a ratchet-engaging portion 94 that extends from the body 92 and engages the ratchet wheel 58 so that the holding pawl 90 is free to ratchet thereon upon rotation of the ratchet wheel 58 in a counter-clockwise direction, as viewed in FIG. 1. It will be understood that the holding pawl 90 is essentially used for the purposes of permitting a selective movement of the ratchet wheel 58, which is a rotation in this invention. An elongated member 96 is disposed on the body 92 generally opposite the ratchet-engaging portion 94 and serves as a seat for a bias member 98 that biases the ratchet-engaging portion 94 for engagement with the ratchet wheel 58. The conventional bias member 98 is caged between an inner surface of the housing 14 and a surface of the holding pawl 90. Thus, the holding pawl 90 moves between a first position where the ratchet wheel 58 is allowed to move in one direction and a second position where the ratchet wheel 58 is allowed to move in an opposite direction.

In further reference to FIGS. 1-2, an optional quick release mechanism may be provided and would includes a release shaft 70 which is journaled in a release shaft bushing 73 perpendicularly secured in the front plate 16 above the driving mechanism 20. A quick release handle 78 is disposed on and secured to an external end of release shaft 70 in a conventional fashion, for example, such as by welding. The release handle 78 may be any one of the presently employed release handles and its detail description will be omitted for the sake of brevity. Advantageously, the body 92 of the holding pawl 90 may be mounted for rotation on the release shaft 70.

In operation, in order to apply the railcar brakes, the hand wheel 22 is rotated in a counter-clockwise direction, as viewed in FIG. 1, and such rotation is transmitted through the drive shaft 24 and the pinion 30 to cause rotation of the gear 32 in the counter-clockwise direction and thereby take-up slack of the force-producing chain 37. Until such time that tension starts to build up in the force-producing chain 37, drive shaft 24, pinion 30, nut 52, and clutch collar 48 all rotate as a unit during rotation of the hand wheel 22. When tension begins to build up in the force-producing chain 37, such tension is reflected in the gear 32 and is transmitted back through the pinion 30 to the clutch collar 48. Resistance to rotation by the clutch collar 48, which is splined to the nut 52, causes the nut 52 to advance on threads 25 and thereby clamp the ratchet wheel 58 between friction surfaces 56 and 57. With the ratchet wheel 58 is so clamped, continued rotation of the hand wheel 22 causes the drive shaft 24, the ratchet wheel 58, and the nut 52 (along with friction plates 59) to rotate as a single unit until the desired tension is attained on the force-producing chain 37, while the holding pawl 90, and more specifically its ratchet engaging-portion 94 ratchets on the ratchet wheel 58. When the desired tension has been attained on the force-producing chain 37, rotation or application of torque on the hand wheel 22 is terminated, and the holding pawl 90 engaged on clamped ratchet wheel 58 prevents the force-producing chain 37 from unwinding, since the holding pawl 90 permits only counter-clockwise rotation of the ratchet wheel 58 of FIG. 1 or clockwise rotation in FIGS. 5A-5C.

Once applied, the railcar brakes (not shown) may be gradually released.

For providing a gradual release of the railcar brakes, the hand wheel 22 is turned clockwise slightly, as viewed in FIG. 1, to partially loosen the nut 52 and thereby reduce the clamping force on the ratchet wheel 58, which is restrained from rotation by the holding pawl 90. The initial clockwise rotation of the hand wheel 22 effects a corresponding rotation of the pinion 30 and the gear 32, thereby easing tension on the chain 37. Continued clockwise rotation of the hand wheel 22 effects complete release of the load on the force-producing chain 37 with the gear 32 continuing to rotate until the winding drum 35 has taken up all chain slack, that is, the amount of chain that had been taken up during the brake-applying phase of operation. When all chain slack has been taken up, further rotation of the gear 32, pinion 30 and nut 52 is terminated with the brakes being fully released. Counter-clockwise rotation of the hand wheel 22 is limited by a drive shaft pin 60 which projects into a slot 61 formed in nut 52.

When optional quick release mechanism is provided, the railcar brakes may be quick released. A quick release of the railcar brake application is caused by rotating the quick release handle 78 (which is normally disposed in an applied position) in a counter-clockwise direction, as viewed in FIG. 1 into a release position.

Figure 4:
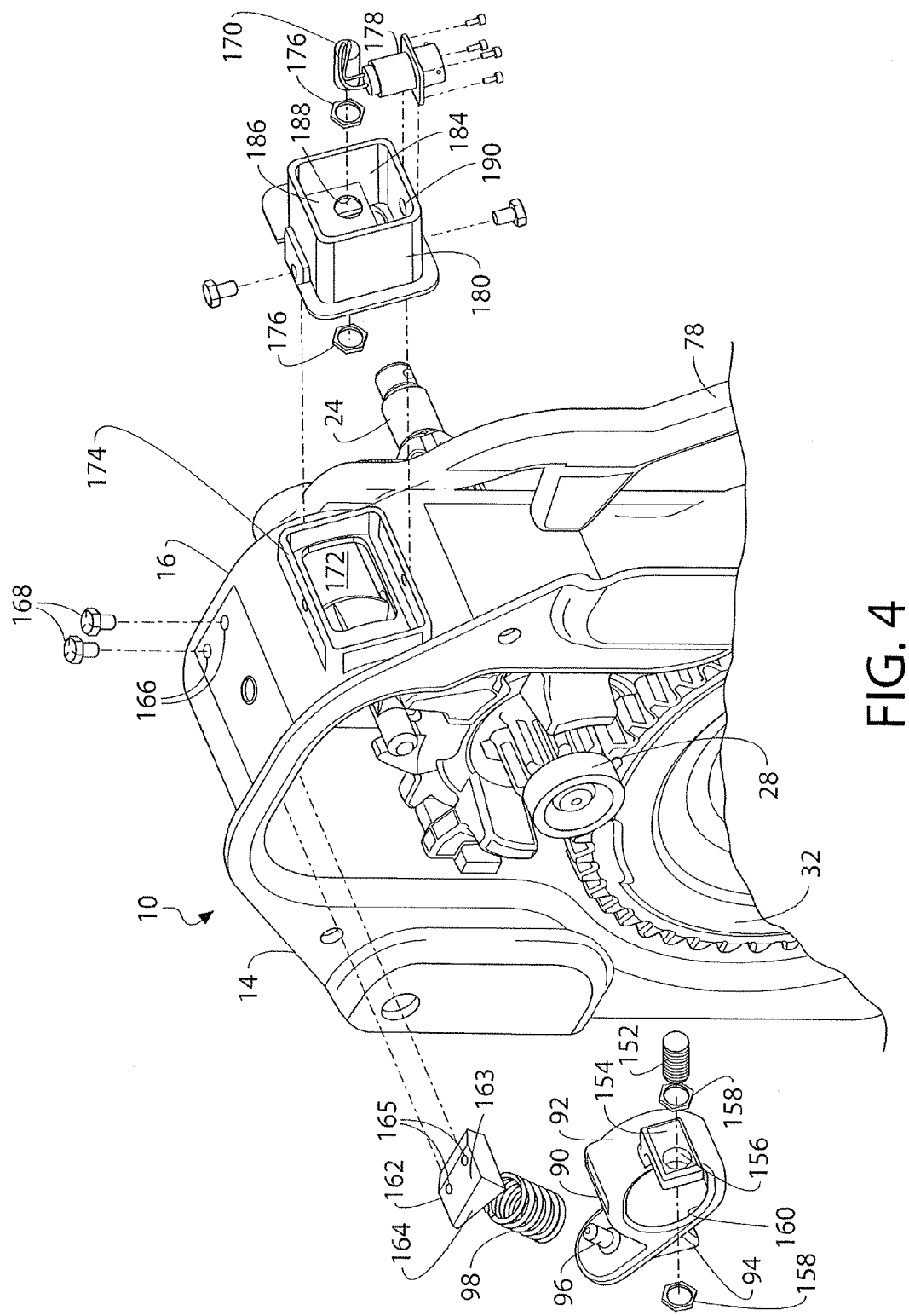
FIG. 4 is an exploded perspective view of the chain tension sensing device in combination with the railroad handbrake of FIGS. 1-3, which is partially illustrated.

Now in reference to FIGS. 4-5c, the instant invention provides a device, generally designated as 150, for sensing at least partially applied condition of the railroad handbrake responsive to a tension attained on the force-producing chain 37. The device 150 includes a member, being a sensor target, 152 mounted in the upper portion of the housing 14 for a generally linear movement during handbrake application and release and a sensor 170 mounted in a position to sense the generally linear movement of the sensor target 152 responsive to one of the at least partially applied and released conditions of the railroad handbrake 10.

The sensor target 152, best shown in FIG. 4, is essentially an elongated member disposed on and attached (secured) to an exterior surface of the body 92 of the holding pawl 90. The sensor target 152 extends in a direction being generally opposite to a direction of the ratchet wheel engaging portion 94 of the holding pawl 90. To attach the sensor target 152 in the instant invention, the holding pawl 90 is provided with a flange 154 secured to and extending from the body 92. The flange 154 has an aperture 156 formed through thickness thereof and sized so as to pass the body of the sensor target 152 therethrough. Advantageously, the body of the sensor target 152 has an external thread allowing the sensor target 152 to be mounted on the flange 154 by way of a pair of threaded nut fasteners 158, essentially caging the thickness of the flange 154 therebetween, although other conventional means of attaching a sensor target to a rigid member are contemplated within the instant invention.

The sensor target 152 is disposed for the generally linear reciprocal movement with the body 92. To achieve such generally linear reciprocal movement, the body 92 of the holding pawl 90 is adapted with an elongated through bore 160 which is formed through a thickness of the body 92 so that the holding pawl 90 is mounted for such generally linear reciprocal movement in a direction being generally transverse to a rotational axis 91 thereof. The sensor target 152 is further generally co-axially aligned with the length of the elongated bore 160, as best shown in FIGS. 4 and 5a-5c. The sensor target 152 is essentially a magnet or has at least a portion thereof having magnetic characteristics.

While the conventional arrangement of the bias member 98 has been found suitable for most applications, the instant invention provides for a longer bias member 98 that can apply a higher force onto ratchet-engaging portion 94 so as to facilitate its engagement with the ratchet wheel 58. Accordingly, there is provided an adapter or member 162 having a surface 163 abutting an inner surface of the housing 14 and an opposed surface 164 that is disposed at an angle relative to the surface 163. A pair of threaded bores or apertures 165 are formed in the surface 163. The housing 14 has a pair of apertures 166 formed through wall thickness thereof in alignment with the threaded bores or apertures 165 so that the adapter 162 can be fastened with a pair of fasteners 168.

The sensor 170 is mounted in a position to sense the generally linear movement of the sensor target 152 responsive to one of the at least partially applied and released conditions of the railroad handbrake 10. Since the holding pawl 90 is mounted for rotation in the upper end of the housing 14, the sensor 170 is then mounted stationary in close proximity to the upper end of the housing 14. The sensor 170 may be of any type and, preferably, the sensor 170 is of a non-contact proximity type. It is further presently preferred for the sensor 170 to be of a reed switch type with the sensor target 152 essentially functioning as a magnet that causes the internal contacts of the switch to pull together and complete electrical circuit (not shown). The advantage of the reed type switch in this application is in that no power is required to operate the sensor 170. The presently preferred sensor 170 is manufactured by Cherry Corporation of Pleasant Prairie, Wis. under the MP2007 series.

By way of an example of FIGS. 1 and 5a-5c, the sensor 170 is mounted on the exterior surface of the housing 14. Accordingly, the housing 14 includes an aperture 172 formed through a wall thickness thereof in a position so that the sensor target 152 passes through the aperture 172 and can be positioned in operative sensing alignment with the sensor 170.

Although the sensor 170 can be mounted in accordance with any conventional methods, there is provided a sensor housing 180 that is generally hollow and that has a pair of open ends 182 and 184. One open end 182 of the sensor housing 180 is secured to the housing 14 by way of at least a peripheral flange 174 upstanding on the exterior surface of the housing 14 in general alignment with and surrounding the aperture 172.

The sensor housing 180 also has a baffle 186 mounted internally between open ends 182 and 184 and having an aperture 188 formed through a thickness thereof. The sensor 170 is then passed through each of the opposed open end 184 and the aperture 188 and is secured to the baffle 186 with a pair of threaded nut fasteners 176. The sensor housing 180 further has an aperture 190 formed though one wall thereof so as to mount an electrical connector 178 in close proximity to the sensor 170 so that the electrical connector 178 is operatively coupled to each of the sensor 170 and the control system (not shown). The electrical connector 178 may be of the type as manufactured by ITT Corporation of White Plaines, N.Y. under Cannon brand, Part Number MS3470W12-3P. However, it is contemplated that the sensor 170 may be directly coupled to the control system (not shown).

The operation of the chain tension sensing device 150 is best shown in FIGS. 5a-5c. FIG. 5a illustrates condition wherein the tension has been at least partially attained on force-producing chain 37 during at least partial application of the railroad handbrake 10, with the sensor target 152 protruding past the exterior surface of the housing 14 through the aperture 172 and being disposed in operative alignment with the sensor 170. In the instant invention, in this operative alignment, the face surface of the sensor target 152 is disposed a predetermined distance from the face surface of the sensor 170. The instant invention takes advantage of a condition within the railroad handbrake 10, wherein tension attained on force-producing chain 37 rotates, for a very small angle, ratchet wheel 58 in the counter-clockwise direction of FIG. 5a when rotation or application of torque on the hand wheel 22 is terminated. This counter-clockwise rotation overcomes the predetermined force of the bias member 98 and moves the body 92 of the holding pawl 90 in a generally linear direction and for a short distance towards the sensor 170 and generally transverse to rotational axis 91 that can be defined by the shaft 70. Subsequently, the generally transverse movement of the body 92 of the holding pawl 90 biases the elongated bore 160 to its one side on the shaft 70 and positions the sensor target 152 in operative sensing alignment with the sensor 170.

While the tension is in a process of being attained on the force-producing chain 37 during at least partial handbrake application, the holding pawl 90 ratchets on the ratchet wheel 58, as illustrated in FIG. 5b, and the predetermined force of the bias member 98 is sufficient to bias or urge the body 92 of the holding pawl 90 for movement towards the ratchet wheel 58. Similarly, when the railroad handbrake 10 is released and tension on the force-producing chain 37 ceases to exist, the bias member 98 biases the ratchet-engaging portion 94 of the holding pawl 90 for engagement with the ratchet wheel 58, as shown in FIG. 5c. In this condition, the sensor target 152 moves away from operative sensing alignment with the sensor 170.

It is important to note that due to the geometry of the ratchet wheel 58 and the holding pawl 90, the axis of the sensor target 152 and the sensor 170 may not be aligned, as best illustrated in FIGS. 5a-5b. Therefore, these components are preselected and the distance therebetween is predetermined so as to accommodate such axial misalignment. Thus, the operative sensing alignment in the instant invention provides for such axial misalignment between the sensor target 152 and the sensor 170.

The sensor 170 is electrically connected to a control circuit (not shown) that is set, in combination, to generate a control signal in response to either sensing or not sensing the sensor target 152. It is presently preferred to generate such control signal when the sensor target 152 is being sensed. It has been found that even partial take-up of the force-producing chain 37 attaining at least partial tension thereon is sufficient to generate the control signal.

Thus, the method for sensing at least partially applied condition of the railroad handbrake 10 includes the step of mounting a sensor target 152 for a reciprocal movement in a generally linear direction during handbrake application and release. Then, mounting a sensor 170 in a position to sense the generally linear movement of the sensor target 152 during at least partial handbrake application. Next, moving the sensor target 152 in the generally linear direction during the at least partial handbrake application. And finally, sensing, with the sensor 170 the generally linear movement of the sensor target 152 during the at least partial handbrake application. The step of mounting the sensor 170 may include a step of mounting such sensor 170 in close proximity to an upper end of the housing 14 of the railroad handbrake 10.

Although, the instant invention has been illustrated and described in combination with a railroad handbrake taught in U.S. Pat. No. 4,368,648, it will be apparent to those skilled in the art, that the instant invention may be applied to other railroad handbrakes employing a ratchet wheel and a holding pawl. For example, such other railroad handbrake is taught in U.S. Pat. No. 4,714,142 issued to Shepherd which uses a differently constructed clutch and release mechanism in combination with a pawl engaging a ratchet wheel disposed within the clutch and release mechanism. Such other handbrake may be also of a quick release type as taught in U.S. Pat. No. 7,757,825 issued to Michel and/or U.S. Pat. No. 7,878,309 issued to Michel et al. These quick release handbrakes are improvements of the handbrake taught in U.S. Pat. No. 4,714,142 and include a clutch with recess and either one pawl 52 with a ratchet wheel engaging portion 53 and clutch engaging portion 54 or a pair of interlocking pawls 52 and 54.

Teachings of U.S. Pat. No. 4,714,142, U.S. Pat. No. 7,757,825 and U.S. Pat. No. 7,878,309 are incorporated into this document by reference thereto.

It will be further apparent to those skilled in the art, that the instant invention may be applied to other devices that employ a chain (or any other elongated force-producing members, such as belts, cords and the like) in combination with a gear and a member allowing selective movement of the gear for the purpose of determining whether or not the tension is present in such force-producing member. Such applications, for example, may be related to a conveyor belt or a cycle chain.

The sensor 170 may be also provided as a limit switch, for example lever actuated, wherein the sensor target 152 will either depress the lever and actuate the switch during at least partial handbrake application or release the lever during handbrake release. The sensor 170 may be also a conventional load cell type device engageable with the end of the sensor target 152 and outputting a value proportional to the pressure applied by the sensor target 152 onto the load cell, the pressure representative of the tension levels attained on the force-producing chain 37. In these arrangements the sensor target 152 does not have to have magnetic characteristics and may be further formed integral with the body 92 of the holding pawl 90.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

I claim:

1. A device for sensing a tension at least partially attained on a force-producing chain of a railroad handbrake, the railroad handbrake having a housing and a chain application and release mechanism at least partially disposed within the housing and including at least a ratchet wheel, a release shaft and a pawl mounted for a rotation thereon and engaging the ratchet wheel, the force-producing chain connected at one end thereof to the chain application and release mechanism and connectable at the opposite end thereof to a brake rigging of a railcar, said device comprising:

(a) an elongated bore formed through a thickness of a body of the pawl so that the pawl is also mounted for a generally linear reciprocal movement in a direction being generally transverse to a rotational axis thereof;

(b) a sensor target disposed on and attached to an exterior surface of the body of the pawl for each of said rotational movement and said generally linear movement during handbrake application and release; and (c) a sensor mounted proximal to an upper portion of the housing in a position to sense said generally linear movement of said sensor target.

2. The device of claim 1, wherein said sensor is electrically coupled to a control system and is operable to generate a control signal in response to sensing or not sensing said generally linear movement of said member.

3. The device of claim 1, wherein the chain application and release mechanism includes a ratchet wheel mounted for a rotation within the housing and a biasing member engaging the body of the pawl, whereby the ratchet wheel moves the body of the pawl in a direction towards said sensor in response to the tension at least partially attained on the force-producing chain during at least partial handbrake application and positions said sensor target in operative sensing alignment with said sensor, and whereby the biasing member moves the body of the pawl in an opposite direction towards the ratchet wheel during handbrake release causing said sensor target to move away from said operative sensing alignment with said sensor.

4. The device of claim 1, wherein said sensor is mounted on an exterior surface of the housing and wherein said device further includes an aperture formed through a thickness of the housing in a position so that said sensor target passes through said aperture for positioning in said operative sensing alignment with said sensor.

5. The device of claim 4, further including a hollow sensor housing disposed on and secured to the exterior surface of the housing, said hollow sensor housing having each of a first open end disposed in general alignment with said aperture formed through a thickness thereof, an opposite second open end and a baffle disposed within said hollow sensor housing between said open ends thereof, said baffle having an aperture formed through a thickness thereof, wherein said sensor is passed through said aperture of said baffle and is secured thereto with a pair of threaded nut fasteners.

6. The device according to claim 1, wherein said sensor target is formed integral with the pawl as a one-piece member.

7. The device of claim 1, further including a flange disposed on and secured to the exterior surface of the body of the pawl, said flange having an aperture formed through a thickness thereof, wherein said sensor target is passed through said aperture formed through said flange and is secured thereto with a pair of threaded nut fasteners.

8. A method for sensing at least partially applied condition of a railroad handbrake, said method comprising the steps of:

(a) mounting a pawl of said railroad handbrake, having an elongated bore and a portion thereof engaging a ratchet wheel of said railroad handbrake, for each of a rotational movement and a reciprocal movement in a generally linear direction during handbrake application and release;

(b) attaching a sensor target to said pawl for said rotational and said reciprocal movements therewith;

(c) mounting a sensor in a position to sense said generally linear reciprocal movement of said sensor target (d) reciprocally moving said sensor target, mounted in step (b) and using said elongated bore, in said generally linear direction; and (e) sensing, with said sensor mounted in step (c), said generally linear movement of said member.

9. The method, according to claim 8, wherein said method includes additional steps of mounting an electrical connector in close proximity to said sensor and the step of operatively coupling said sensor to said electrical connector.

10. The method, according to claim 8, wherein step (c) includes steps of mounting said sensor on an exterior surface of a housing of said handbrake and forming an aperture through a thickness of said housing in a general alignment with said sensor target.

11. The method, according to claim 8, wherein step (c) includes a step of mounting said sensor and said sensor target proximal an upper end of a housing of said railroad handbrake.

12. The method, according to claim 8, wherein each of steps (d) and (e) includes a step of attaining tension on a force-producing chain of said railroad handbrake.

13. The method, according to claim 8, wherein step (b) includes a step of disposing said sensor target on and attaching said sensor target to an exterior surface of said pawl.

14. The method, according to claim 8, wherein said method includes an additional step of operatively coupling said sensor to a control system.

15. A device for sensing a tension at least partially attained on a force-producing chain of a railroad handbrake, the railroad handbrake having a housing and a chain application and release mechanism at least partially disposed within the housing and including at least a ratchet wheel, a release shaft and a pawl mounted for a rotation thereon and having a portion thereof engaging the ratchet wheel, the force-producing chain connected at one end thereof to the chain application and release mechanism and connectable at an opposite end thereof to a brake rigging of a railcar, said device comprising:

(a) a sensor target disposed on the pawl and extending in a direction being opposite to a direction of the ratchet wheel engaging portion of the pawl, said sensor target rotating with the pawl and moving with the pawl in a generally linear direction during application and release of the railroad handbrake;

(b) a sensor mounted proximal to an upper portion of the housing in a position to sense said generally linear movement of said sensor target responsive to one of at least partially applied and released conditions of the railroad handbrake;

(c) an elongated bore formed through a thickness of the pawl and receiving the release shaft therewithin, said sensor target being co-axially aligned with a length of said elongated bore;

(d) an aperture formed through a thickness of the housing, said sensor target being received within said aperture and protruding past an exterior surface of the housing toward said sensor when the tension has been at least partially attained on the force-producing chain; and (e) a hollow sensor housing disposed on and secured to the exterior surface of the housing, said hollow sensor housing having each of a first open end disposed in general alignment with said aperture formed through a thickness thereof, an opposite second open end and a baffle disposed within said hollow sensor housing between said open ends thereof, said baffle having an aperture formed through a thickness thereof, wherein said sensor is passed through said aperture of said baffle and is secured thereto with fasteners.

16. The device of claim 15, wherein said sensor is a non-contact proximity sensor.

17. The device of claim 15, wherein said sensor is a reed switch and wherein said sensor target is a magnet.

18. The device of claim 15, wherein said sensor is a limit switch.

19. The device of claim 15, wherein said elongated bore is biased to one side thereof on the release shaft, when a rotation or an application of a torque on a hand wheel of the railroad handbrake is terminated, whereby said sensor target is positioned in an operative sensing alignment with said sensor.

20. The device of claim 19, wherein said elongated bore is biased to an opposite side thereof on the release shaft when a tension on the force-producing chain is in a process of being attained and when the ratchet engaging portion of the pawl is biased for engagement with the ratchet wheel, whereby said sensor target is positioned away from said sensor.

21. The device of claim 15, wherein said sensor is a load cell outputting a value proportional to a pressure applied by said sensor target onto said load cell.

22. The device of claim 15, wherein said sensor generates a control signal upon sensing said sensor target when the tension has been at least partially attained on the force-producing chain.

23. The device of claim 15, further comprising an electrical connector coupled to each of said sensor and a control system.

24. The device of claim 15, wherein said sensor is directly coupled to a control system.

25. A method for sensing a tension condition on a force-producing chain of a railroad handbrake, said method comprising:
 providing a device composing a pawl mounted within said railroad handbrake in an engagement with a ratchet wheel of said railroad handbrake and including an elongated bore, a sensor target attached to said pawl and being co-axially aligned with a length of said elongated bore and a sensor mounted in a position to sense said sensor target;
 reciprocally moving, said sensor target, during a rotation of said pawl, in a generally linear direction using said elongated bore; and
 generating, with said sensor, a control signal when said sensor is sensing or not sensing said target during said generally linear movement thereof, said control signal defining said tension condition.

* * * * *